United States Patent
Wang et al.

(10) Patent No.: US 9,840,473 B1
(45) Date of Patent: Dec. 12, 2017

(54) METHOD OF PREPARING A HIGH PURITY IMIDAZOLIUM SALT

(71) Applicant: Evonik Degussa GmbH, Essen (DE)

(72) Inventors: Xinming Wang, Kanagawa-ken (JP);
Olivier Zehnacker, Dortmund (DE);
Benjamin Willy, Düsseldorf (DE); Rolf Schneider, Gründau-Rothenbergen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/619,567

(22) Filed: Jun. 12, 2017

(30) Foreign Application Priority Data

Jun. 14, 2016 (EP) ..................................... 16174303

(51) Int. Cl.
*C07D 233/56* (2006.01)
*C07F 9/141* (2006.01)

(52) U.S. Cl.
CPC ............ *C07D 233/56* (2013.01); *C07F 9/141* (2013.01)

(58) Field of Classification Search
None
See application file for complete search history.

(56) References Cited

U.S. PATENT DOCUMENTS

| | | | |
|---|---|---|---|
| 1,882,258 A | 10/1932 | Randel |
| 2,516,625 A | 7/1950 | Haury |
| 2,601,673 A | 6/1952 | McMillan et al. |
| 2,802,344 A | 8/1957 | Witherell |
| 3,276,217 A | 10/1966 | Boume et al. |
| 3,317,654 A | 5/1967 | Yonkers |
| 3,580,759 A | 5/1971 | Albertson et al. |
| 3,609,087 A | 9/1971 | Chi et al. |
| 4,079,263 A | 3/1978 | Inoue |
| 4,094,957 A | 6/1978 | Sartori et al. |
| 4,106,904 A | 8/1978 | Oude Alink et al. |
| 4,112,051 A | 9/1978 | Sartori et al. |
| 4,152,900 A | 5/1979 | Chopra et al. |
| 4,152,901 A | 5/1979 | Munters |
| 4,201,721 A | 5/1980 | Hallgren |
| 4,217,238 A | 8/1980 | Satori et al. |
| 4,251,494 A | 2/1981 | Say |
| 4,360,363 A | 11/1982 | Ferrin et al. |
| 4,405,579 A | 9/1983 | Sartori et al. |
| 4,405,586 A | 9/1983 | Sartori et al. |
| 4,466,915 A | 8/1984 | Lai |
| 4,489,563 A | 12/1984 | Kalina |
| 4,524,587 A | 6/1985 | Kantor |
| 4,525,294 A | 6/1985 | Sartori et al. |
| 4,605,743 A | 8/1986 | Malz et al. |
| 4,643,000 A | 2/1987 | Rheinfelder |
| 4,701,530 A | 10/1987 | Swearingen et al. |
| 4,714,597 A | 12/1987 | Trevino |
| 4,889,938 A | 12/1989 | Kristen et al. |
| 5,016,445 A | 5/1991 | Wehr |
| 5,126,189 A | 6/1992 | Tanny et al. |
| 5,186,009 A | 2/1993 | Rockenfeller |
| 5,186,010 A | 2/1993 | Wehr |
| 5,255,534 A | 10/1993 | Ryan |
| 5,303,565 A | 4/1994 | Pravada |
| 5,390,509 A | 2/1995 | Rockenfeller et al. |
| 5,873,260 A | 2/1999 | Linhardt et al. |
| 6,117,963 A | 9/2000 | Boinowitz et al. |
| 6,128,917 A | 10/2000 | Riesch et al. |
| 6,130,347 A | 10/2000 | Julius et al. |
| 6,155,057 A | 12/2000 | Angell et al. |
| 6,165,433 A | 12/2000 | Chakravarti et al. |
| 6,184,433 B1 | 2/2001 | Harada et al. |
| 6,423,282 B1 | 7/2002 | Araki et al. |
| 6,475,370 B2 | 11/2002 | Lehmann et al. |
| 6,672,099 B1 | 1/2004 | Yoshimi et al. |

(Continued)

FOREIGN PATENT DOCUMENTS

| CA | WO 2004016631 A1 * | 2/2004 | ........... C07C 305/06 |
|---|---|---|---|
| CA | 2 817 704 | 5/2012 | |

(Continued)

OTHER PUBLICATIONS

Blachly, et al., "Stabilization of Monoethanolnsine Solutions in Carbon Dioxide Scrubbers," *J. Chem. Eng. Data* 11(3):401-403 (Jul. 1966).
Call,"Aminoxyle - eine Klasse stablier," *Pharmazie in unserer Zeit* 3:83-95 (Jan. 1977); with English language translation attached.
Kirchhoff, et al., "Triacetoneamine Derivatives Industrial Applications and Recent Developments," pp. 1-9, Addcon World '99 (Two-Day Conference, Oct. 1999).
Lewin, et al., "Molecular Features Associated with Polyamine Modulation of NMDA Receptors," *J Med. Chem.* 41:988-995 (published online Feb. 1998).
Luo, et al., "Dehumidification performance of [Emevi]BF$_4$," *Applied Thermal Engineering* 3104-151:2772-2777 (Oct. 2011).

(Continued)

*Primary Examiner* — Michael Barker
(74) *Attorney, Agent, or Firm* — Law Office of: Michael A. Sanzo, LLC

(57) ABSTRACT

The present invention encompasses a novel method for synthesizing highly pure salts of the general formula $Q^+A^-$, wherein $Q^+$ is:

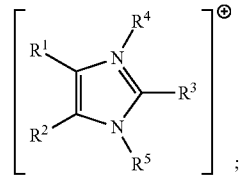

and wherein $A^-$ is

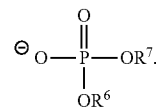

20 Claims, No Drawings

(56) References Cited

U.S. PATENT DOCUMENTS

| | | |
|---|---|---|
| 6,680,047 B2 | 1/2004 | Klaveness et al. |
| 6,727,015 B1 | 4/2004 | Putter et al. |
| 7,419,646 B2 | 9/2008 | Cadours et al. |
| 7,435,318 B2 | 10/2008 | Arlt et al. |
| 7,638,636 B2 | 12/2009 | Zhou et al. |
| 7,666,813 B2 | 2/2010 | Hoefer et al. |
| 7,754,053 B2 | 7/2010 | Maase |
| 7,827,820 B2 | 11/2010 | Weimer et al. |
| 7,998,714 B2 | 8/2011 | Gellett et al. |
| 8,069,687 B2 | 12/2011 | Jork et al. |
| 8,167,983 B2 | 5/2012 | Seiler et al. |
| 8,277,615 B2 | 10/2012 | Ruffert et al. |
| 8,318,117 B2 | 11/2012 | Lichtfers et al. |
| 8,357,344 B2 | 1/2013 | Bouillon et al. |
| 8,362,095 B2 | 1/2013 | Schwab et al. |
| 8,382,962 B2 | 2/2013 | Massonne et al. |
| 8,470,079 B2 | 6/2013 | Agar et al. |
| 8,500,867 B2 | 8/2013 | Seiler et al. |
| 8,500,892 B2 | 8/2013 | Seiler et al. |
| 8,506,839 B2 | 8/2013 | Shiflett et al. |
| 8,523,978 B2 | 9/2013 | Rojey et al. |
| 8,623,123 B2 | 1/2014 | Seiler et al. |
| 8,696,928 B2 | 4/2014 | Seiler et al. |
| 8,703,451 B2 | 4/2014 | Haas et al. |
| 8,715,521 B2 | 5/2014 | Shiflett et al. |
| 8,784,537 B2 | 7/2014 | Seiler et al. |
| 8,809,576 B2 | 8/2014 | Schraven et al. |
| 8,932,478 B2 | 1/2015 | Seiler et al. |
| 9,221,007 B2 | 12/2015 | Rolker et al. |
| 9,630,140 B2 | 4/2017 | Willy et al. |
| 2004/0016631 A1 | 1/2004 | Madkour |
| 2004/0133058 A1 | 7/2004 | Arlt et al. |
| 2005/0070717 A1 | 3/2005 | Wasserscheid et al. |
| 2005/0129598 A1 | 6/2005 | Chinn |
| 2005/0164082 A1 | 7/2005 | Kishi et al. |
| 2005/0202967 A1 | 9/2005 | Hoefer et al. |
| 2005/0245769 A1 | 11/2005 | Kohler et al. |
| 2006/0104877 A1 | 5/2006 | Cadours et al. |
| 2006/0150665 A1 | 7/2006 | Weimer et al. |
| 2006/0197053 A1 | 9/2006 | Shiflett et al. |
| 2006/0251961 A1 | 11/2006 | Olbert et al. |
| 2007/0004903 A1 | 1/2007 | Hoff et al. |
| 2007/0095645 A1 | 5/2007 | Masse |
| 2007/0144186 A1 | 6/2007 | Shiflett et al. |
| 2007/0264180 A1 | 11/2007 | Carrette et al. |
| 2007/0286783 A1 | 12/2007 | Carrette et al. |
| 2008/0028777 A1 | 2/2008 | Boesmatm et al. |
| 2008/0114105 A1 | 5/2008 | Hell et al. |
| 2008/0283383 A1 | 11/2008 | Ruffert et al. |
| 2009/0029121 A1 | 1/2009 | Hammermami et al. |
| 2009/0029887 A1 | 1/2009 | Schwab et al. |
| 2009/0036334 A1 | 2/2009 | Schwab et al. |
| 2009/0139232 A1 | 6/2009 | Collis |
| 2009/0170734 A1 | 7/2009 | Schwab et al. |
| 2009/0199709 A1 | 8/2009 | Rojey et al. |
| 2009/0211447 A1 | 8/2009 | Lichtfers et al. |
| 2010/0011958 A1 | 1/2010 | Cadours et al. |
| 2010/0016205 A1 | 1/2010 | Schwab |
| 2010/0029519 A1 | 2/2010 | Schwab et al. |
| 2010/0071557 A1 | 3/2010 | Seiler et al. |
| 2010/0084597 A1 | 4/2010 | Schwab et al. |
| 2010/0086983 A1 | 4/2010 | Gellett et al. |
| 2010/0095703 A1 | 4/2010 | Jork et al. |
| 2010/0104490 A1 | 4/2010 | Bouillon et al. |
| 2010/0132551 A1 | 6/2010 | Bouillon et al. |
| 2010/0186590 A1 | 7/2010 | Vorberg et al. |
| 2010/0288126 A1 | 11/2010 | Agar et al. |
| 2010/0300870 A1 | 12/2010 | Massonne et al. |
| 2010/0326126 A1 | 12/2010 | Seiler et al. |
| 2011/0000236 A1 | 1/2011 | Seiler et al. |
| 2011/0081287 A1 | 4/2011 | Bouillon et al. |
| 2011/0094381 A1 | 4/2011 | Lichtfers et al. |
| 2011/0118504 A1 | 5/2011 | Haas et al. |
| 2011/0135549 A1 | 6/2011 | Lichtfers et al. |
| 2011/0185901 A1 | 8/2011 | Jacquin et al. |
| 2011/0247494 A1 | 10/2011 | Dinnage et al. |
| 2011/0256043 A1 | 10/2011 | Blair et al. |
| 2011/0309295 A1 | 12/2011 | Joh et al. |
| 2012/0011886 A1 | 1/2012 | Shiflett et al. |
| 2012/0017762 A1 | 1/2012 | Seiler et al. |
| 2012/0080644 A1 | 4/2012 | Seiler et al. |
| 2012/0117991 A1 | 5/2012 | Rached |
| 2012/0247144 A1 | 10/2012 | Seiler et al. |
| 2012/0308458 A1 | 12/2012 | Seiler et al. |
| 2012/0315366 A1 | 12/2012 | Zehnacher et al. |
| 2013/0011314 A1 | 1/2013 | Porcheron et al. |
| 2013/0023712 A1 | 1/2013 | Porchenon et al. |
| 2013/0031930 A1 | 2/2013 | Seiler et al. |
| 2013/0031931 A1 | 2/2013 | Seiler et al. |
| 2013/0118350 A1 | 5/2013 | Rolker et al. |
| 2013/0133327 A1 | 5/2013 | Milam et al. |
| 2013/0219949 A1 | 8/2013 | Seiler et al. |
| 2013/0247758 A1 | 9/2013 | Seiler et al. |
| 2013/0263743 A1 | 10/2013 | Seiler et al. |
| 2013/0327084 A1 | 12/2013 | Shiflett et al. |
| 2014/0005344 A1 | 1/2014 | Rinker et al. |
| 2014/0090558 A1 | 4/2014 | Rolker et al. |
| 2014/0105801 A1 | 4/2014 | Rolker et al. |
| 2014/0120016 A1 | 5/2014 | Rolker et al. |
| 2014/0356268 A1 | 12/2014 | Schraven et al. |
| 2014/0360369 A1 | 12/2014 | Schraven et al. |
| 2015/0024106 A1 | 1/2015 | Huller et al. |
| 2015/0024247 A1 | 1/2015 | Lockett et al. |
| 2015/0125373 A1 | 5/2015 | Willy et al. |
| 2015/0175738 A1 | 6/2015 | Willy et al. |
| 2015/0175740 A1 | 6/2015 | Willy et al. |
| 2015/0308720 A1 | 10/2015 | Zelmacker et al. |
| 2015/0321139 A1 | 11/2015 | Schraven et al. |
| 2016/0045857 A1 | 2/2016 | Rolker et al. |
| 2016/0115827 A1 | 4/2016 | Rached |
| 2016/0153318 A1 | 6/2016 | Busse et al. |
| 2016/0175766 A1 | 6/2016 | Zelmacker et al. |

FOREIGN PATENT DOCUMENTS

| | | |
|---|---|---|
| CN | 1076380 A | 9/1993 |
| CN | 102335545 | 2/2012 |
| DE | 400 488 | 8/1924 |
| DE | 633 146 | 7/1936 |
| DE | 737031 | 7/1943 |
| DE | 36 23 680 A1 | 1/1988 |
| DE | 266 799 A1 | 4/1989 |
| DE | 195 11 709 | 10/1996 |
| DE | 103 33 546 | 2/2005 |
| DE | 10 2004 053 167 | 5/2006 |
| DE | 10 2010 001 070 | 7/2011 |
| DE | 10 2010 004 779 | 7/2011 |
| DE | 10 2011 055 859 | 6/2013 |
| DE | 10 2013 010 035 | 12/2014 |
| DE | 10 2014 214 670 | 1/2016 |
| DE | 10 2014 214 674 | 1/2016 |
| DE | 10 2014 214 682 | 1/2016 |
| DE | 10 2015 212 749 | 1/2017 |
| DE | 10 2016 210 481 | 6/2017 |
| EP | 0 033 529 A1 | 1/1981 |
| EP | 0 047 967 | 9/1981 |
| EP | 0 079 767 | 5/1983 |
| EP | 0 187 130 | 7/1986 |
| EP | 0 193 327 | 9/1986 |
| EP | 0 302 020 | 2/1989 |
| EP | 0 558 019 | 2/1993 |
| EP | 2 636 715 | 9/2013 |
| FR | 670 497 | 11/1929 |
| FR | 2 900 841 A1 | 11/2007 |
| GB | 1 306 853 | 2/1973 |
| GB | 1 501 195 | 2/1978 |
| GB | 2 047 681 | 12/1980 |
| GB | 2 528 494 | 1/2016 |
| JP | 33-009879 B | 11/1958 |
| JP | 57-191407 | 11/1982 |
| JP | 61-129019 | 6/1986 |
| JP | 62-73055 | 4/1987 |
| JP | 1-134180 | 5/1989 |
| JP | 2-298767 | 12/1990 |

(56) References Cited

FOREIGN PATENT DOCUMENTS

| | | |
|---|---|---|
| JP | 4-268176 | 9/1992 |
| JP | 6-307730 | 11/1994 |
| JP | 7-167521 | 7/1995 |
| JP | 2001-219164 | 8/2001 |
| JP | 2002-047258 | 2/2002 |
| JP | 2004-44945 | 2/2004 |
| JP | 2006-239516 | 9/2006 |
| JP | 2006-282525 | 10/2006 |
| JP | 2013-051238 | 3/2013 |
| RU | 2 101 625 | 1/1998 |
| RU | 2 122 642 | 11/1998 |
| RU | 2 183 003 | 5/2002 |
| WO | WO 93/13367 | 7/1993 |
| WO | WO 00/61698 A1 | 10/2000 |
| WO | WO 2002/016671 | 2/2002 |
| WO | WO 2004/016631 | 2/2004 |
| WO | WO 2004/082809 | 9/2004 |
| WO | WO 2006/012097 | 2/2006 |
| WO | WO 2006/048182 | 5/2006 |
| WO | WO 2007/099041 | 9/2007 |
| WO | WO 2009/074535 | 6/2009 |
| WO | WO 2009/133059 | 11/2009 |
| WO | WO 2010/037109 | 4/2010 |
| WO | WO 2011/131552 | 10/2011 |
| WO | WO 2012/110987 | 8/2012 |
| WO | WO 2012/150051 | 11/2012 |
| WO | WO 2013/041300 | 3/2013 |
| WO | WO 2013/050230 | 4/2013 |
| WO | WO 2013/050242 | 4/2013 |
| WO | WO 2013/072147 | 5/2013 |
| WO | WO 2015/000637 | 1/2015 |
| WO | WO 2017/005538 | 1/2017 |

OTHER PUBLICATIONS

Luo, et al., "Investigation of feasibility of ionic liquids used in solar liquid desiccant air conditioning system," *Solar Energy* 86(9):2781-2724 (Sep. 2012).
Satori, et al.,"Sterically Hindered Amines for $CO_2$ Removal from Gases," *Ind. Eng. Chem. Fundam.* 22(2):239-249 (accepted Jan. 1983).
Gerald Scott, Develpoments in polymer stabilization-5, Chapter 3: Antioxidant action of sterically hindered amines and related compounds, Shlyapintokh and Ivanor; pp. 41-70, Applied Science Publishers (1982).
Shao & Stangeland, "Amines Used in $CO_2$ Capture—Health and Environmental Impacts," Bellona Report (Sep. 2009).
Ulmann's Encyclopedia of Industrial Chemistry, 5th Edition, vol. 83, "Antioxidants" pp. 91-104 (1985).
Wellner, et al., "Entwässerung ionischer Flüssigkeiten in einem Fallfilmverdampfer," *Chemie Ingenieur Technik* 83(9):1493-1501(Jul. 2011); with complete English language translation.
Yunus, "Gaslöslichkeit in ionischen Flüssigkeiten," IsoSORP Application Note Nr. 4:1-2 (Feb. 2014); with complete English language translation.
Encylopedia of Chemical Process and Design, Ed. John J. McKetta, vol. 32. Marcel Deckker, Inc. (1990) pp. 123-126.
Kanakubo, et al., "$CO_2$ solubility in and physical properties for ionic liquid mixtures of 1-butyl-3-methylimidazolium acetate and 1-butyl-3-methylimidazolium bis(trifluoromethanesulfonyl)amide," *Journal of Molecular Liquids* 217:112-119 (2016); available online Feb. 12, 2016.
Krannich, et al., "Characterization of Six Hygroscopic Ionic Liquids with Regard to Their Suitability for Gas Dehydration: Density, Viscosity, Thermal and Oxidative Stability, Vapor Pressure, Diffusion Coefficient, and Activity Coefficient of Water," *Journal of Chemical Engineering &Data* 61:1162-1176 (Feb. 2016).
Kriebel, et al., "Absorption, 2. Design of Systems and Equipment," Uhnann's Encyclopedia of Industrial Chemistry, vol. 1, pp. 75-90 (2008).
Lall-Ramnarine, et al., "Probing the Physical Properties, Synthesis and Cellulose Dissolution Ability of Dialkyl Phosphate Ionic Liquids," *Phosphorous, Sulfur, and Silicon* 190:891-895 (2015).
Lungwitz, Ralf, "Ionische Flüssigkeiten—Polarität und Wechselwirkungen mit silikatischen Oberflächen," Dissertation Technische Universitat Chemnitz (Nov. 2011); with English language translation of relevant parts.
English language translation of Mao, et al., "Development and Application of New Technique for Recovery of Low Partial Pressure Carbon Dioxide," *Journal of Chemical Industry & Engineering* 25(3):12-15 (Jun. 2004).
English language translation of Rolker, et al., "Separation of carbon dioxide from flue gases by means of absorption," *Chemie Ingenieur Tecknik* 78(4):416-424 (Jul. 2006).
OECD Guidelines for the Testing of Chemicals, Test No. 104, items 14-19, (adopted May 1981).
Projekt der Deutschen Bundesstiftung: Gasreinigung mit ionischen Flüssigkeiten Umwelt; Endbericht (Sep. 2009); with English language translation of relavant parts.
English language translation of Xiao, "Study on Technique for Recovery of Carbon Dioxide from Flue Gas," *Modern Chemical Industry* 24(5):47-49 (May 2004).
European Search Report completed Jul. 21, 2016 for counterpart European application EP 16 17 4303.
U.S. Appl. No. 14/124,472, filed Dec. 6, 2013, 2014-0090558 A1, Apr. 3, 2014, Rolker.
U.S. Appl. No. 14/373,350, filed Jul. 19, 2014, 2014-0356268 A1, Dec. 4, 2014 Schraven.
U.S. Appl. No. 14/973,084, filed Dec. 17, 2015, 2016-0175766 A1, Jun. 23, 2016, Zehnacker.
U.S. Appl. No. 15/486,300, filed Apr. 13, 2017, Bahlmann.
U.S. Appl. No. 15/619,561, filed Jun. 12, 2017, Irfan.
U.S. Appl. No. 15/619,566, filed Jun. 12, 2017, Willy.
U.S. Appl. No. 15/619,573, filed Jun. 12, 2017, Zehnacker.
U.S. Appl. No. 15/619,577, filed Jun. 12, 2017, Zehnacker.
U.S. Appl. No. 15/619,584, filed Jun. 12, 2017, Zehnacker.
"Mutual Solubility of Water and Pyridine Derivatives" by Richard M. Stephenson, *J. Chem. Eng. Data* 38, p. 428-431, (Jul. 1993).
"Review of Organic Functional Groups: Introduction to Medicinal Organic Chemistry" by Thomas L. Lemke, Lippincott Williams & Wilkins, p. 40 (2003).
"Review of Organic Functional Groups: Introduction to Medicinal Organic Chemistry" by Thomas L. Lemke, Lippincott Williams & Wilkins, p. 39 (2003).
Brennecke, et al., "Ionic Liquids: Innovative Fluids for Chemical Processing," *AIChE Journal* 47(11):2384-2389 (Nov. 2001).
Chua, et at, "Improved Thermodynamic Property Fields of LiBr-$H_2O$ Solution," *International Journal of Refrigeration* 23:412-429 (Sep. 2000).
De Lucas, et al., "Vapor Pressures, Densities, and Viscosities of the (Water + Lithium Bromide + Lithium Formate) System and (Water + Lithium Bromide + Potassium Formate) System," *Journal of Chemical and Engineering Data, American Chemical Society, US* 48(1):18-22 (Jan. 2003).
De Lucas, et al., "Absolution of Water Vapor into Working Fluids for Absorption Refrigeration Systems," *Industrial & Engineering Chemistry Research, American Chemical Society, US* 46(1):345-350 (2007); (published online Dec. 2006).
Domanska, et al., Solubility of 1-Alkyl-3-ethylimidazolium-Based Ionic Liquids in Water and 1-Octanol, *J. Chem. Eng. Data* 53:1126-1132 (Apr. 2008).
Galán, et al., "Solvent Properties of Functionalized Ionic Liquids for $CO_2$ Absorption," *IChemE* 85(A1):31-39 (Jan. 2007).
Glebov, et al., "Experimental Study of Heat Transfer Additive Influence on the Absorption Chiller Performance," *International Journal of Refrigeration* 25:538-545 (Aug. 2002).
Kim, et al., "Surface tension and viscosity of 1-butyl-3-methylimidazolium iodide and 1-buty1-3- methylimidazolium tetrafluoroborate, and solubility of lithium bromide+1-butyl-3-methylimidazolium bromide in water," *Korean J. Chem. Eng.* 23(1):113-116 (Jan. 2006).

(56) References Cited

OTHER PUBLICATIONS

Kim, et al., "Performance Evaluation of Absorption Chiller Using $LiBr + H_2N(CH_2)_2OH + H_2O$, $LiBr + HO(CH_2)_3OH + H_2O$, and $LiBr + (HOCH_2CH_2NH + H_2O$ as Working Fluids," *Applied Thermal Engineering* 19:217-225 (Feb. 1999).

Kim, et al., "Refractive Index and Heat Capacity of 1-Butyl-3-Methylimidazolium Bromide and 1-Butyl-3-Methylimidazolium Tetrafluoroborate, and Vapor Pressure of Binary Systems for 1-Butyl-3-Methylimidazolium Tetrafluoroborate-Trifluoroethanol," *Fluid Phase Equilibria* 218:215-220 (Apr. 2004).

Li, et al., "Correlation and Prediction of the Solubility of $CO_2$ and $H_2S$ in an Aqueous Solution of 2-Piperidineethanol and Sulfolane," *Ind. Eng. Chem. Res.* 37:3098-3104 (May 1998).

Liu, et al., the physical properties of aqueous solution of room-temperature ionic liquids based on imidazolium:Database and Evaluation, *J. Mol. Liquids* 140:68-72 (Jan. 2008).

Mitsubishi Heavy Industries, Ltd., "Flue Gas $CO_2$ Recovery Technology and Its Application to EOR: an Effective Strategy for Addressing the Issues of Global Warming and Peaking Oil Supply," vol. 44, p. 20-23 (2007).

Perez-Blanco, "A Model of an Ammonia-Water Falling Film Absorber," *ASHRAE Transactions* vol. 94, pp. 467-483, 1988; Presented at the winter meeting in Dallas Texas of the American Society of Heating, Refrigerating and Air-Conditioning Engineers, Inc. (1988).

Wasserscheid, et al., "Ionic Liquids—New "Solutions" for Transition Metal Catalysis," *Angew. Chem. Int. Ed.* 39:3772-3789 (Nov. 2000).

Wu, et al., "Novel Ionic Liquid Thermal Storage for Solar Thermal Electric Power Systems," *Proceeding of Solar Forum. Solar Energy: The Power to Choose* (Apr. 21-25, 2001).

Yoon, et al., "Cycle Analysis of Air-Cooled Absorption Chiller Using a New Working Solution," *Energy* 24:795-809 (Sep. 1999).

Zhang, et al., "Screening of ionic Liquids to Capture CO2 by COSMO-RS and Experiments," *AIChE Journal* 54(10):2171-2728 (Oct. 2008).

Zhou, The Vapor Surfactant Theory of Absorption and Condensation Enhancement, *Proc. Int. Sorption Heat Pump Conference*, (Sep. 24-27, 2002).

Ziegler, et al., "Heat-Transfer Enhancement by Additives," *International Journal of Refrigeration* 19:301-309 (Jun. 1996).

Ziegler, et al., "Multi-effect absorption chillers," *Rev. Int. Froid* 16(5):301-311 (1993).

Ziegler, et al., "Recent developments and future prospects of sorption heat pump systems," *Int. J. Therm. Sci.* 38:191-208 (Mar. 1999).

\* cited by examiner

METHOD OF PREPARING A HIGH PURITY IMIDAZOLIUM SALT

CROSS REFERENCE TO RELATED APPLICATIONS

The present application claims priority under 35 USC §119 to European application, EP16174303.4, filed on Jun. 14, 2016, the contents of which is incorporated herein by reference in its entirety.

FIELD OF THE INVENTION

The invention relates to a method of preparing a high purity imidazolium salt.

BACKGROUND OF THE INVENTION

In air conditioning systems for the aeration and conditioning of buildings or vehicles, the air generally not only has to be cooled, but also dehumidified since the air to be cooled often has such a high humidity that, upon cooling to the desired temperature, the dew point is fallen below. Hence in conventional air conditioning systems dehumidification of the air accounts for a large part of the electricity consumption.

One option of reducing the electricity consumption of air conditioning systems for buildings is the dehumidification of air by adsorption or absorption of water using a drying medium and a regeneration of the drying medium laden with water by heating to a temperature at which the water is desorbed again. Compared to adsorption on a solid adsorbent, the advantage of absorption in a liquid absorption medium is that drying of air can be performed with reduced equipment complexity and with less drying medium and that regeneration of the water-laden drying medium using solar heat is easier to carry out.

The aqueous solutions of lithium bromide, lithium chloride or calcium chloride hitherto employed as liquid absorption media in commercial air conditioning systems have the disadvantage that they are corrosive towards the metallic materials of construction typically employed in air conditioning systems and that they thus necessitate the use of expensive specific materials of construction. These solutions can additionally cause problems due to salt crystallizing out of the absorption medium.

Ionic liquids comprising dialkylimidazolium ions (as described in WO 2004/016631 A1) have been described as alternatives to lithium salts in the prior art for similar applications. Y. Luo et al., Appl. Thermal Eng. 31 (2011) 2772-2777 proposes the ionic liquid 1-ethyl-3-methylimidazolium tetrafluoroborate in place of aqueous solutions of lithium bromide for drying of air.

Y. Luo et al., Solar Energy 86 (2012) 2718-2724 proposes the ionic liquid 1,3-dimethyimidazolium acetate as an alternative to 1-ethyl-3-methylimidazolium tetrafluoroborate for drying of air.

US 2011/0247494 A1 proposes, in paragraph [0145], the use of trimethylammonium acetate or 1-ethyl-3-methylimidazolium acetate as liquid drying agent instead of aqueous lithium chloride solution. Example 3 compares water uptake from humid air for a series of further ionic liquids.

However, a problem of ionic liquids comprising dialkylimidazolium ions is that they often comprise impurities, which lead to substances that are odour-intensive or are injurious to health entering the dehumidified air upon a dehumidification of air using the ionic liquid. Moreover, it has been found that during the desorption of water from ionic liquids which contain a basic anion, such as, for example, a carboxylate ion, odour-intensive decomposition products are formed which, in the event of a subsequent use of the ionic liquid for the dehumidification of air, enter the dehumidified air.

Therefore, there remains a need for ionic liquids comprising imidazolium ions, which do not display the disadvantages described above. The problem to be solved by the present invention is hence provision of a process for the production of ionic liquids comprising dialkylimidazolium ions, wherein the level of volatile compounds is brought to a minimum.

DETAILED DESCRIPTION OF THE INVENTION

It has been surprisingly found that the above problem is solved by the process described hereinafter.

The invention hence provides a process for preparing a high purity compound of formula (I):

$$Q^+A^-,$$

wherein $Q^+$ is

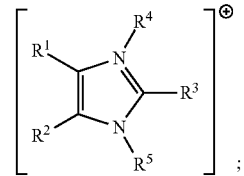

and wherein $A^-$ is

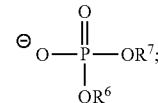

the process comprising:
a) reacting a compound of formula (II) with a compound of formula (III), wherein (II) and (III) are:

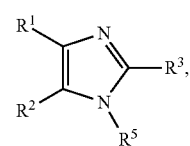

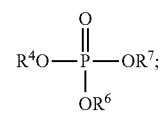

to give a crude product comprising a compound of formula (I);
b) adding water to the crude product of formula (I) from step a), to give a diluted crude product comprising a compound of formula (I);
c) at least partial removal of the water added in step b) from the diluted crude product by distillation of the diluted crude product at a temperature $T_1$ in the range of 30-180° C. and at a pressure $p_1$ which is lower than the saturated vapour pressure of compound (III) at the temperature $T_1$, giving a high purity compound of formula (I);

wherein:

each of $R^1$, $R^2$, $R^3$ are independently a hydrogen or alkyl of 1 to 4 carbon atoms, each of $R^4$, $R^5$, $R^6$, $R^7$ are independently alkyl of 1 to 4 carbon atoms.

In a preferred embodiment of the present invention, $R^1$=$R^2$=$R^3$=hydrogen and each of $R^4$, $R^5$, $R^6$, $R^7$ are independently methyl or ethyl. In a more preferred embodiment of the present invention, $R^1$=$R^2$=$R^3$=hydrogen, $R^5$=methyl and each of $R^4$, $R^6$, $R^7$ are independently methyl or ethyl. In an even more preferred embodiment of the present invention, $R^1$=$R^2$=$R^3$=hydrogen, $R^5$=methyl and $R^4$=$R^6$=$R^7$=ethyl.

In step a) of the process according to the invention, a compound of formula (II) with a compound of formula (III) is reacted, giving a crude product comprising a compound of formula (I). The skilled person is familiar with the reaction conditions, which are described in WO 2004/016631 A1, for example.

In particular, step a) of the process according to the invention is preferably carried out at a temperature in the range of from 130° C. to 200° C., more preferably 140° C. to 190° C., even more preferably 150° C. to 175° C.

The pressure of the reaction is not critical and may be for example atmospheric pressure, preferably under an inert atmosphere, such as nitrogen.

As the reaction is exothermic, it may be desirable to control the rate of addition in some cases and/or to apply external cooling during the addition step.

In general, the compounds of formula (II) and (III) are present in stoichiometric amounts, i.e. the molar relation of compound (II) to compound (III) is in the range 0.9:1 to 1.1:1, more preferably 1:1. In some cases, it might be advantageous to use the imidazole compound (II) in a slight excess to the phosphate ester (III), for example in the range of 1.01 to 1.4 molar equivalents, preferable 1.02 to 1.4.

The reaction time is not particularly limited. Typically, the reaction is continued until at least 90% of the compounds (II) or (III) has reacted to form compound (I). The progress of the reaction can be conveniently controlled by methods known to the skilled person, such as NMR The reaction in step a) can be carried out in the presence or absence of a solvent and is preferably carried out in the absence of a solvent.

"Solvent" means water or organic solvents which are known to the skilled person, preferably it means water. These organic solvents are preferably selected from the group consisting of aliphatic solvents, preferably pentane, hexane, heptane, octane, decane, cyclohexane, tetramethylsilane; aromatic solvents, preferably benzene, toluene, xylene; ether compounds, preferably diethyl ether, dipropyl ether, dibutyl ether, methyl tert-butyl ether; halogenated solvents, preferably dichloromethane, chloroform, tetrachloromethane; alcohols, preferably methanol, ethanol, propanol, iso-propanol, butanol, tert-butanol; esters, preferably methyl acetate, ethyl acetate, propyl acetate, butyl acetate; acetone. Especially preferred organic solvents are selected from esters, alcohols.

"Absence of a solvent" means particularly that the overall content of all solvents in the reaction mixture is below 10 weight-% based on the sum of the weights of compounds (II) and (III), preferably below 5 weight-% based on the sum of the weights of compounds (II) and (III), more preferably below 1 weight-% based on the sum of the weights of compounds (II) and (III).

"Presence of a solvent" means that the sum of all solvents present in the reaction mixture is at least 1.0 weight-%, based on the combined masses of compounds (II) and (III). Even more preferred, it means that the sum of all solvents present in the reaction mixture is at least 3.7 weight-%, based on the combined masses of compounds (II) and (III). Even more preferred, it means that the sum of all solvents present in the reaction mixture is at least 7.4 weight-%, based on the combined masses of compounds (II) and (III). Even more preferred, it means that the sum of all solvents present in the reaction mixture is at least 10.0 weight-%, based on the combined masses of compounds (II) and (III). Even more preferred, it means that the sum of all solvents present in the reaction mixture is at least 20.0 weight-%, based on the combined masses of compounds (II) and (III). Even more preferred, it means that the sum of all solvents present in the reaction mixture is at least 40.0 weight-%, based on the combined masses of compounds (II) and (III). Even more preferred, it means that the sum of all solvents present in the reaction mixture is at least 80 weight-%, based on the combined masses of compounds (II) and (III). Even more preferred, it means that the sum of all solvents present in the reaction mixture is at least 100 weight-%, based on the combined masses of compounds (II) and (III). Even more preferred, it means that the sum of all solvents present in the reaction mixture is at least 150 weight-%, based on the combined masses of compounds (II) and (III).

In the embodiment of the invention in which the step a) is carried out in the presence of a solvent, it is preferred that the solvent is at least partially removed after step a) before step b) is carried out. Such at least partial removal can be carried out by extraction, stripping, distillation or any other process known to the skilled person, preferably by extraction, stripping, distillation. In this context, "partial removal" means in particular, that at least 50% of the solvent added in step a) is removed, preferably at least 70%, even more preferably at least 90%, even more preferably 99% of the solvent is removed.

In case step a) is carried out in the presence of a solvent comprising water, the partial removal of the solvent is preferably carried out by distillation at a temperature $T_2$ in the range of 30-180° C., preferably 37° C.-178° C., even more preferably 50° C.-150° C., even more preferably 60° C.-120° C., even more preferably 70° C.-99° C., and at a pressure $p_2$ which is lower than the saturated vapour pressure of compound (III) at the temperature $T_2$.

In a preferred embodiment, the pressure $p_2$ is also higher than the saturated vapour pressure of the compound (I), even more preferably higher than the saturated vapour pressure of a mixture of compound (I):water=99:1, even more preferably 98:2, even more preferably 97:3.

The result of the reaction of step a) of the method according to the invention is a crude product comprising a compound of formula (I).

Within the context of the invention, the term "crude product" means the reaction mixture which is obtained after the reaction has taken place [step a) of the process according to the invention] and is then submitted to step b). As stated above, in case step a) is carried out in presence of a solvent, such solvent can be optionally removed at least partially from the crude product obtained after step a) before step b) is carried out.

The crude product obtained in step a) is then further processed in step b). In step b), water is added to the crude product of formula (I) from step a), preferably in an amount of at least 1 weight-% based on the amount of compounds (II) and (III) used in step a), giving a diluted crude product comprising a compound of formula (I).

Preferably, in step b) water is added to the crude product of formula (I) from step a) in an amount in the range of 1 to 200, more preferably 5 to 100, even more preferably 7 to 75, even more preferably 10 to 50, most preferably 15 to 20 weight-% based on the amount of compounds (II) and (III) used in step a).

Within the context of the invention, the term "diluted crude product" means the mixture which is obtained after the addition of water according to step b) and is then submitted to step c).

In step c) of the process, the water added in step b) is then at least partially removed from the diluted crude, wherein special temperature and pressure conditions are applied. Namely, it is essential to the invention that the water is removed by distillation at a temperature $T_1$ in the range of 30-180° C., preferably 37° C.-178° C., even more preferably 50° C.-150° C., even more preferably 60° C.-120° C., even more preferably 70° C.-99° C., and at a pressure $p_1$ which is lower than the saturated vapour pressure of compound (III) at the temperature $T_1$.

"At least partially removed" in the context of the invention with respect to claim c) means, that at least 50% of the water added in step b) is removed, preferably at least 70%, even more preferably at least 90%, even more preferably 99% of the water added in step b) is removed.

For carrying out the distillation, all apparatuses known to the person skilled in the art can be used, thus e.g. a stirred reactor, a falling-film evaporator or a thin-film evaporator, in each case in combination with a suitable distillation column or another apparatus suitable for the distillation.

The pressure $p_1$ at which the distillation takes place has to be lower than the saturated vapour pressure of compound (III) at the temperature $T_1$, wherein $T_1$ is in the range of 30-180° C.

In a preferred embodiment, the pressure $p_1$ is also higher than the saturated vapour pressure of the compound (I), even more preferably higher than the saturated vapour pressure of a mixture of compound (I):water=99:1, even more preferably 98:2, even more preferably 97:3.

"Saturated vapour pressure" of a certain substance or mixture is defined as the pressure exerted by a vapour of this substance or mixture in thermodynamic equilibrium with its condensed phases (solid or liquid) at a given temperature in a closed system.

The saturated vapour pressure at the respective temperature can be determined by the skilled person by methods known in the art. For example, and according to the invention, the saturated vapour pressures of a certain substance or mixture is determined as set forth in the OECD Guidelines for the Testing of Chemicals (1981): Test No. 104, items 14-19 "Static Method", adopted Mar. 23, 2006.

In a preferred embodiment of the method according to the present invention, steps b) and c) are carried out at least twice, even more preferably at least three times, wherein step b) is carried out with the high purity compound of formula (I) obtained in directly antecedent step c).

It has now surprisingly been found that, only when the combination of the water addition step b) and the distillation step c) according to the method of the invention is carried out, the product obtained at the end of step c) has as unexpectedly low level of odour-intensive and smelly substances. This is even more surprising as a skilled person would not have treated the crude product (I) obtained after step a) with water, especially because compound (I) is in fact to be used as water-absorbing material.

The method of the present invention thus provides as a product a highly pure imidazolium salt.

The following examples illustrate the invention.

EXAMPLES

Materials

In the following examples, N-methylimidazole (CAS number: 616-47-7) and triethylphosphate (CAS number: 78-40-0) were purchased from Sigma Aldrich.

Methods

The saturated vapour pressures were determined by the method described in: OECD Guidelines for the Testing of Chemicals (1981): Test No. 104, items 14-19 "Static Method", adopted Mar. 23, 2006.

The saturated vapour pressure determined by this method for triethylphosphate follow the formula <1> wherein $$\log_{10}(p) = 16.42 - 5108.4/(273.15 + T) \qquad <1>.$$

In formula <1>, p is the pressure in hPa, T is the temperature in ° C., "$\log_{10}$" is the common logarithm.

The saturated vapour pressure of triethylphosphate at 150° C.=22268 hPa, at 140° C.=11363 hPa, at 120° C.=2669.9 hPa, at 99° C.=493.5, at 85° C.=143.5 hPa, at 70° C.=34.1 hPa, at 60° C.=12.2 hPa, at 50° C.=4.1 hPa.

The saturated vapour pressure of a mixture of 99 parts of 1-ethyl-3-methylimidazolium diethylphosphate (=EMIM DEP) and 1 part of water are as follows: at 150° C.=380 hPa, at 140° C.=254 hPa, at 85° C.=18.6 hPa, at 60° C.=4.2 hPa.

The residuals in each sample were determined by olfactory analysis.

In addition, the residuals in samples obtained in V1-V4 and E1-E3 were determined by headspace GC/MS as follows: 0.1 g of the sample was incubated for 20 minutes at 70° C. in a sampler. The composition of the gas phase was analyzed directly with gas chromatography ("GC") and mass spectrometry ("MS"). GC is performed with an apparatus of Hewlett Packard ("HP 6890"; sampler: Turbomatrix 40, Perkin Elmer). MS is performed with an apparatus of Hewlett-Packard ("HP 5973").

The quantity of the residuals are determined based on the peak height observed in the chromatogram.

General Procedure for Inventive Examples E1-E8 and Comparative Examples V1-V8

Triethylphosphate (929 g, 5.0 mole) was added dropwise to a reaction vessel containing N-methylimidazole (411 g, 5.0 mole). Afterwards the reaction mixture was heated up to 150° C. and stirred under reflux for 14 h. Then, the mixture was diluted with 20 weight-% of water (based on the sum of the masses of the starting materials triethylphosphate and N-methylimidazole) and the water was distilled of at different pressures as summarized in the following table.

In comparative example V1, the treatment with water was omitted and the mixture merely moved to a rotary evaporator.

In all examples except V1, 93.8 g water (=7 weight-% based on the combined masses of triethylphosphate and N-methylimidazole used in the general procedure) were added. In examples V2-V4, the water was removed at 60° C. and a pressure of 20 hPa, which is above the saturated vapour pressure of triethylphosphate at the respective temperature (12.2 hPa).

In example V5, the water was removed at 50° C. and a pressure of 5 hPa, which is above the saturated vapour pressure of triethylphosphate at the respective temperature (4.1 hPa).

In example V6, the water was removed at 60° C. and a pressure of 14 hPa, which is above the saturated vapour pressure of triethylphosphate at the respective temperature (12.2 hPa).

In example V7, the water was removed at 70° C. and a pressure of 37 hPa, which is above the saturated vapour pressure of triethylphosphate at the respective temperature (34.14 hPa).

In example V8, the water was removed at 99° C. and a pressure of 540 hPa, which is above the saturated vapour pressure of triethylphosphate at the respective temperature (493.5 hPa).

In inventive examples E1-E3, water was added, and the water was removed at 60° C. (E1, E2) or 85° C. (E3) and a pressure of 5 and 20 hPa, respectively, which is below the saturated vapour pressure of triethylphosphate at the respective temperatures (12.2 hPa at 60° C. and 143.5 hPa at 85° C.).

In example E4, the water was removed at 50° C. and a pressure of 3 hPa, which is below the saturated vapour pressure of triethylphosphate at the respective temperature (4.1 hPa).

In example E5, the water was removed at 60° C. and a pressure of 10 hPa, which is below the saturated vapour pressure of triethylphosphate at the respective temperature (12.2 hPa).

In example E6, the water was removed at 70° C. and a pressure of 31 hPa, which is below the saturated vapour pressure of triethylphosphate at the respective temperature (34.1 hPa).

In example E7, the water was removed at 99° C. and a pressure of 440 hPa, which is below the saturated vapour pressure of triethylphosphate at the respective temperature (493.5 hPa).

In example E8, the water was removed at 120° C. and a pressure of 1000 hPa, which is below the saturated vapour pressure of triethylphosphate at the respective temperature (2669.9 hPa).

| Example | Water added? | Distillation at T [°C.]/p [hPa] | Repetitions of adding water und distillation | Residual [ng/g] | odor |
|---|---|---|---|---|---|
| V1 | No | 150/50 | 0 | 3049 | sweet and slightly fishy |
| V2 | Yes | 60/20 | 1 | 1021 | slightly fishy |
| V3 | Yes | 60/20 | 2 | 407 | slightly fishy |
| V4 | Yes | 60/20 | 3 | 297 | very slightly fishy |
| V5 | Yes | 50/5 | 1 | | slight sweet |
| V6 | Yes | 60/14 | 1 | | slight sweet |
| V7 | Yes | 70/37 | 1 | | slight sweet |
| V8 | Yes | 99/540 | 1 | | slight sweet |
| E1 | Yes | 60/5 | 1 | 70 | No smell |
| E2 | Yes | 60/5 | 3 | n.d.* (<10) | No smell |
| E3 | Yes | 85/20 | 3 | n.d.* (<10) | No smell |
| E4 | Yes | 50/3 | 1 | | No smell |
| E5 | Yes | 60/10 | 1 | | No smell |
| E6 | Yes | 70/31 | 1 | | No smell |
| E7 | Yes | 99/440 | 1 | | No smell |
| E8 | Yes | 120/1000 | 1 | | No smell |

* "n.d." = "not detectable"

The above summarized result show that only when the combination of the water addition step b) and the removal step c), only when carried out under the distillation conditions according to the invention, lead to the highly pure imidazolium salt.

All references cited herein are fully incorporated by reference. Having now fully described the invention, it will be understood by those of skill in the art that the invention may be practiced within a wide and equivalent range of conditions, parameters and the like, without affecting the spirit or scope of the invention

What is claimed is:

1. A process for preparing a high purity compound of formula (I): $Q^+A^-$,
   wherein $Q^+$ is:

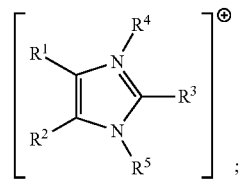

and wherein $A^-$ is:

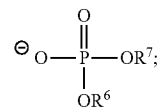

the process comprising:
   a) reacting a compound of formula (II) with a compound of formula (III), wherein (II) and (III) are:

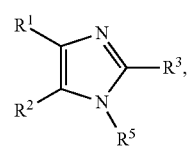

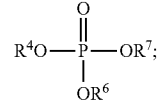

to give a crude product comprising a compound of formula (I);
   b) adding water to the crude product of formula (I) from step a), to give a diluted crude product comprising a compound of formula (I);
   c) at least partial removal of the water added in step b) from the diluted crude product by distillation of the diluted crude product at a temperature $T_1$ in the range of 30-180° C. and at a pressure $p_1$ which is lower than the saturated vapour pressure of compound (III) at the temperature $T_1$, giving a high purity compound of formula (I);
   wherein:
   each of $R^1$, $R^2$, $R^3$ are independently a hydrogen or alkyl of 1 to 4 carbon atoms;
   each of $R^4$, $R^5$, $R^6$, $R^7$ are independently alkyl of 1 to 4 carbon atoms.

2. The process of claim 1, wherein $R^1=R^2=R^3=$hydrogen and wherein each of $R^4$, $R^5$, $R^6$, $R^7$ are independently methyl or ethyl.

3. The process of claim 2, wherein $R^1=R^2=R^3=$hydrogen, $R^5=$methyl and wherein each of $R^4$, $R^6$, $R^7$ are independently methyl or ethyl.

4. The process of claim 1, wherein step a) is carried out in the absence of a solvent.

5. The process of claim 1, wherein step a) is carried out in the presence of a solvent.

6. The process of claim 5, wherein the solvent is at least partially removed between steps a) and b).

7. The process of claim 1, wherein, in step b), water is added in an amount of at least 1 weight-% based on the amount of compounds (II) and (III) used in step a).

8. The process of claim 1, wherein "partial removal" in step c) means removal of at least 50% of the water added in step b).

9. The process of claim 1, wherein pressure $p_1$ is lower than the saturated vapour pressure of compound (III) at the temperature $T_1$ and higher than the saturated vapour pressure of (I) at the temperature $T_1$.

10. The process of claim 1, wherein steps b) and c) are carried out at least twice, and wherein step b) is carried out with the high purity compound of formula (I) obtained in directly antecedent step c).

11. The process of claim 2, wherein said process is carried out in the absence of an organic solvent.

12. The process of claim 11, wherein in step b) water is added in an amount of at least 1 weight-% based on the amount of compounds (II) and (III) used in step a).

13. The process of claim 12, wherein "partial removal" in step c) means removal of at least 50% of the water added in step b).

14. The process of claim 13, wherein pressure $p_1$ is lower than the saturated vapour pressure of compound (III) at the temperature $T_1$ and higher than the saturated vapour pressure of (I) at the temperature $T_1$.

15. The process of claim 14, wherein steps b) and c) are carried out at least twice, and wherein step b) is carried out with the high purity compound of formula (I) obtained in directly antecedent step c).

16. The process of claim 3, wherein said process is carried out in the absence of an organic solvent.

17. The process of claim 16, wherein in step b) water is added in an amount of at least 1 weight-% based on the amount of compounds (II) and (III) used in step a).

18. The process of claim 17, wherein "partial removal" in step c) means removal of at least 50% of the water added in step b).

19. The process of claim 18, wherein pressure $p_1$ is lower than the saturated vapour pressure of compound (III) at the temperature $T_1$ and higher than the saturated vapour pressure of (I) at the temperature $T_1$.

20. The process of claim 19, wherein steps b) and c) are carried out at least twice, and wherein step b) is carried out with the high purity compound of formula (I) obtained in directly antecedent step c).

* * * * *